(12) United States Patent
Shachar et al.

(10) Patent No.: US 12,076,527 B2
(45) Date of Patent: Sep. 3, 2024

(54) METHOD AND APPARATUS FOR A LONG-TERM, FULLY IMPLANTABLE MRI COMPATIBLE DRUG PUMP

(71) Applicant: Cognos Therapeutics Inc., Los Angeles, CA (US)

(72) Inventors: Yehoshua Shachar, Santa Monica, CA (US); Winston Wu, Alhambra, CA (US)

(73) Assignee: Cognos Therapeutics Inc., Inglewood, CA (US)

( * ) Notice: Subject to any disclaimer, the term of this patent is extended or adjusted under 35 U.S.C. 154(b) by 842 days.

(21) Appl. No.: 16/397,623

(22) Filed: Apr. 29, 2019

(65) Prior Publication Data

US 2020/0338325 A1 Oct. 29, 2020

(51) Int. Cl.
*A61M 5/142* (2006.01)
*A61M 5/168* (2006.01)
*A61M 5/172* (2006.01)
*A61M 27/00* (2006.01)

(52) U.S. Cl.
CPC .... *A61M 5/14276* (2013.01); *A61M 5/16831* (2013.01); *A61M 5/16881* (2013.01); *A61M 5/172* (2013.01); *A61M 27/002* (2013.01); *A61M 2005/14208* (2013.01); *A61M 2005/16863* (2013.01); *A61M 2205/3306* (2013.01); *A61M 2205/3344* (2013.01); *A61M 2205/3368* (2013.01); *A61M 2205/3553* (2013.01); *A61M 2205/3584* (2013.01); *A61M 2205/50* (2013.01); *A61M 2205/52* (2013.01); *A61M 2205/7518* (2013.01)

(58) Field of Classification Search
CPC ........................ A61M 5/14276; A61M 27/002
See application file for complete search history.

(56) References Cited

U.S. PATENT DOCUMENTS

| 8,323,270 | B2* | 12/2012 | Shachar | C07K 16/22 |
|---|---|---|---|---|
| | | | | 604/891.1 |
| 2002/0173773 | A1* | 11/2002 | Olsen | A61M 5/14276 |
| | | | | 604/151 |
| 2004/0078027 | A1 | 4/2004 | Shachar | |
| 2004/0176818 | A1* | 9/2004 | Wahlstrand | A61N 1/37518 |
| | | | | 607/45 |

(Continued)

FOREIGN PATENT DOCUMENTS

| WO | 2011037838 | 3/2011 |
|---|---|---|
| WO | 2012128998 | 9/2012 |

(Continued)

*Primary Examiner* — Jenna Zhang
(74) *Attorney, Agent, or Firm* — Marcus C. Dawes

(57) ABSTRACT

The illustrated embodiments of the invention include an MRI compatible apparatus having: a refillable drug reservoir; a hermetically sealed, implantable chamber; a pump disposed in and hermetically sealed within the hermetically sealed, implantable chamber and fluidically communicated to the drug reservoir; and control electronics disposed in and hermetically sealed within the hermetically sealed, implantable chamber and electrically communicated to the pump. The refillable drug reservoir, hermetically sealed, implantable chamber, pump and control electronics are MRI compatible.

27 Claims, 13 Drawing Sheets

(56) References Cited

U.S. PATENT DOCUMENTS

| | | | |
|---|---|---|---|
| 2006/0036286 A1* | 2/2006 | Whitehurst | A61B 5/415 |
| | | | 607/3 |
| 2009/0318902 A1 | 12/2009 | Shachar | |
| 2009/0318903 A1* | 12/2009 | Shachar | A61M 5/16827 |
| | | | 604/891.1 |
| 2012/0245565 A1* | 9/2012 | Shachar | A61M 5/14276 |
| | | | 604/891.1 |
| 2013/0101527 A1* | 4/2013 | Llinas | B82Y 5/00 |
| | | | 424/48 |
| 2017/0325685 A1* | 11/2017 | Shachar | A61B 5/4839 |

FOREIGN PATENT DOCUMENTS

| | | | |
|---|---|---|---|
| WO | 2017117138 | 7/2017 | |
| WO | WO-2017117138 A1 * | 7/2017 | A61M 1/14 |

\* cited by examiner

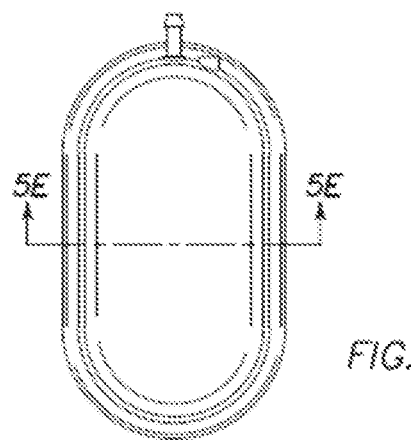
FIG. 5D
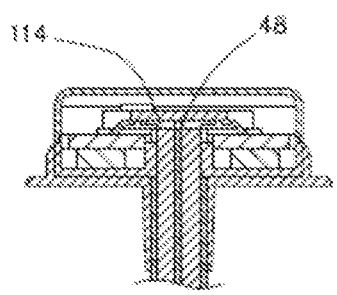
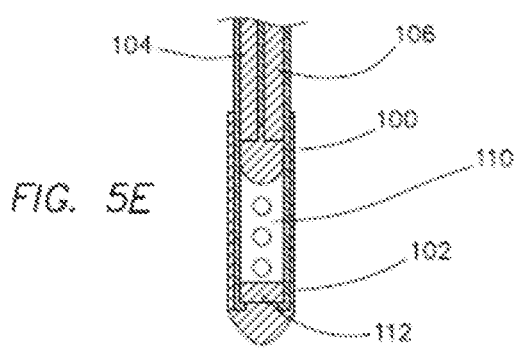
FIG. 5E

METHOD AND APPARATUS FOR A LONG-TERM, FULLY IMPLANTABLE MRI COMPATIBLE DRUG PUMP

BACKGROUND

Field of the Invention

The present invention relates generally to implantable medical devices, and more particularly to an improved, MRI compatible and hermetically sealed, infusion pump incorporating a piezoelectric pump mechanism for use in local administration of biological response modifiers and chemotherapeutic agents in tumor fighting.

Description of the Prior Art

The underlying hypothesis of using cytotoxic drug is that more is better. Thus, a first step in administrating a cytotoxic agent is to determine the maximum tolerated dose (MTD). However, when used in traditional treatment modes, such as chemotherapy, the cytotoxic agents are delivered to the patient in a manner that allows the cytotoxic agents to be distributed systemically throughout the body of the patient. Relatively large doses of the drugs are required since only a small fraction of the administered dose will be present at the tumor site at any given time. The remainder of the dose will be in other parts of the body. Moreover, a major problem with conventional chemotherapy is the lack of specificity of the cancer cell.

The use of large doses of toxic agents often leads to serious and debilitating side effects. Moreover, the global administration of drugs is often not compatible with combination therapies where several medicating agents are used synergistically to treat tumors or other conditions. Thus, the global administration of medicating agents to treat tumors and other such medical conditions is an inefficient, often dangerous, technique that often leads to severe or debilitating side effects.

The current generation of infusion pumps in market place has four limitations. First, they use electromagnetic pump systems whose operations are sensitive to intense magnetic radiation from magnetic resonance imaging (MRI). The use of MRI is routine for cancer patients, so these pumps are not suitable for cancer patients. Second, these infusion pumps have peristaltic pumping mechanism that is prone to leaking from the flexible tubing. This peristaltic pumping mechanism cannot be hermetically sealed, leading to corrosion inside the pumps after long implantation times. Third, these pumps do not have wireless communication for monitoring and adjustment of dosage. The delivery rate is set mechanically at the time of implantation. Finally, these pumps do not have feedback sensors to monitor the concentration of medication after delivery. The rate of delivery is constant and cannot be adjusted based on how well medication is absorbed at the point of delivery.

SUMMARY OF INVENTION

A method and apparatus for local infusion of a variety of medicating agents such as biological response modifiers (BRMs) and chemotherapeutic agents is described. In one embodiment, this device contains a magnetic resonance (MR) safe pumping and valve mechanism for use in patients who need to be in a magnetic resonance imaging (MRI) instrument.

In one embodiment, this device is hermetically sealed between drug and non-drug chambers inside the pump, as well as between the pump and patient body, to prevent corrosion to pump control mechanisms and electronics for long-term, full implantation.

In one embodiment, an electronic system provides accurate regulation of administration of such medicating agents by using an optical sensor to monitor the concentration of medicating agents in the tumor site.

In one embodiment, a wireless communication system provides the capability to monitor, track, and adjust the delivery of medicating agents. This method and apparatus are designed with cancer patients in mind but can be used for any form medication that requires local delivery. The operation of the pump is remotely programmable to adjust the delivery of medicating agents.

The illustrated embodiments of the present invention solves the above mentioned problems and other problems by providing a system and method for dispensing medicating agents, controlling, regulating, and reporting the results of such agents at the tumor site of a patient. One embodiment provides a system where monitoring and reporting of biological response parameters are maintained in the resident memory of the system.

One embodiment includes an implantable piezoelectric layer-wise pump and valve for use in local administration of medicating agents.

In one embodiment, an implantable apparatus is used to assist in improving the art of dispensing medication to tumors with an effective use of the agents (BRMs Chemo, TNF, and others) in a definite dose and timeline to produce tumor burden elimination or reduction.

In one embodiment, medicating agents include agents, such as biological response modifiers, enzymes, therapeutic agents, drugs, chemotherapy agents, and the like.

One embodiment is configured to enhance the mechanism of vectoral change of the tumor escape mechanism by introducing enough tumor antigen to stimulate the immune system of the patient.

One embodiment is configured to assist in irrigating a solid tumor by increasing the number of cell adhesion molecules which are used for the adherence of cytotoxic cells to target tumor cells before lysis can ensue, because the malignant cells cannot bind to cytotoxic cells thereby escaping immune surveillance. The embodiment is also configured to assist in irrigating a solid tumor by increasing the number of local administration of cytotoxic cells by the use of the apparatus will improve and enhance such a process.

One embodiment is configured to administrate biological response modifiers (BRMs) with an improved dose, local delivery and scheduling on a case specific basis using a programmable microcontroller and its associated valve mechanism.

One embodiment is configured to allow the clinician the ability to prescribe an optimal biological dose (OBD) as opposed to maximum tolerated dose (MTD) using a control mode defined by its programmability and its logic, which is embedded in the microcontroller look-up-tables.

One embodiment is configured to incorporate the pharmacokinetic and pharmacodynamic parameters associated with chemotherapeutic agents to achieve the desired results without the toxic side effects known to those familiar with the art.

One embodiment is configured to modulate and modify the output of the medicating agents during treatment by changing the procedure in real time using a command structure of the microcontroller look-up-tables with the use of a communication link built into the apparatus.

One embodiment is configured to regulate the rate of dispensation of the medicating agents by modifying the duty cycle of the pump or valve located in the apparatus.

One embodiment is configured to regulate the intake of the tumor BRMs due to their pleiotropic nature and allow for biological processes and mechanisms to develop by selectively reducing or enhancing the various agents in the medication reservoir, hence providing a treatment specific to the patient (e.g. tumor size, lysis, etc.).

One embodiment is configured to control and regulate capabilities to provide actions specific within a time domain such as the introduction of interferon alpha to tumor site (INF-2), whose immune modulating effects and/or anti-proliferate effects and dosing can be very different depending on which effect is to be maximally stimulated.

One embodiment is configured to provide maximum dosing of chemotherapeutic agents to the tumor site by using the maximum tolerated doses (MTD) in a time domain which does not interfere with the activity of BRMs using the selective control of the piezo actuating mechanism built in the apparatus.

One embodiment is configured to provide the clinician a way to allow the expression of BRMs cascade effects (due to the communication of cytokines as messengers with their synergistic, additive or antagonistic interactions that affect the target tumor cells).

One embodiment is configured to provide scheduling of medicating agents such as chemotherapy and BRMs based on their toxicity, and to allow for measures such as bioavailability, solubility, concentration, and circulation based on locality, which scheduling, measures and circulation are improved approaches to the elimination solid tumors.

One embodiment is configured to address the individual differences of various tumors based on the disease stage, immune factors, body weight, age and chronobiology through the ability of the apparatus to locally administer the agents, dosing and scheduling.

One embodiment is configured to mitigate the known factors such as peak serum concentration, (generally associated with peak occurrence of side effects on IFN intravenously injected, which serves as a typical model) whereby the peak concentration of IFN is correlated clinically with peak side effects.

One embodiment is configured to support clinical studies and to demonstrate that responses to BRMs such as IFN gamma follow a bell-shaped response curve whereby when the concentration of the drug increases so does its response, hence the availability of the apparatus with its local administration of drug delivery affords an improved use of such processes.

One embodiment is configured to provide an effective mode of administrating BRMs with chemotherapy as a combination therapy by making available a local administration of different IFNs with IL-2, or IL-2 in combination with monoclonal antibodies and tumor necrosis factors (TFNs), and scheduling by using the said invention.

One embodiment is configured to enable drug manufacturers to evaluate the effectiveness of its drugs during animal and clinical studies by providing the details and feedback on the use, dose, cycle, circadian time effects and the entire pharmacokinetic and pharmacodynamic behavior of medicating agents not as verbal reports of symptomology chronicles by the patient but as a biological measure of tumor responses to the agents.

One embodiment is configured to implant the apparatus near the tumor site for effective local delivery of the medicating agents.

One embodiment is configured to provide a method and apparatus for local administration of BRMs and chemotherapeutic agents, to enhance mechanisms that support overlapping effects in reducing tumor burden and elimination of tumors. To induce an improved response by using biomodulators (augmenting the patients anti-tumor response via production of cytokines), decreasing suppressor mechanisms, increasing the patient's immunological response, limiting the toxicity of such agents (by the locality), maximizing the dose, increasing susceptibility of cells membrane characteristics for improved chemotherapy results at the site, and decreasing the tumors ability to metastasize.

The above characteristics are measurable elements as dosing and scheduling improves the effectiveness of chemotherapy on malignant cells and reduces the exposure of such toxins to normal tissues.

One embodiment provides improved immunomodulation with relatively little immuno-suppression.

One embodiment can be used by a variety of clinical techniques such as the Creech technique of regional or isolated limb perfusion to administer high-doses of chemotherapy to an isolated site of melanoma or sarcoma. This technique is used by BRMs and TNF-α have anti-tumor effects by damaging the neovascular circulation surrounding tumors without destroying normal tissue. The fact that the effective use of TNF-α cannot be administered systemically due to its toxic effects (septic shock) is just a model for the varieties of cytotoxic as well as chemotherapeutic agents, hence the use of local administration by the apparatus is beneficial.

One embodiment provides for defining an improved dose and schedule of biological agents to maximize the anti-tumor effects of each agent while not increasing toxicity to the patient. Treatment modality by using combination therapy and local administration of such agents on a specific schedule is one of the benefits of the invention.

BRIEF DESCRIPTION OF THE DRAWINGS

The various features of the present invention and the manner of attaining them will be described in greater detail with reference to the following description, claims, and drawings, wherein like reference numerals are used, where appropriate, to indicate a correspondence between the referenced items.

FIG. 5d is a top plan view of the shunt of FIG. 5a in a second azimuthal orientation parallel with the page rotated 90° with respect to the orientation of FIG. 5b.

FIG. 5e is a side cross sectional view of the shunt of FIG. 5a as seen through section lines B-B of FIG. 5d. The shunt contains an intraventricular catheter, which connects to the pump chamber.

FIG. 8a is a top perspective view of the system with the case cap removed showing section lines 8b-8b.

FIG. 8b is a side cross sectional view of the system as seen through section lines 8b-8b of FIG. 8a.

FIG. 9a is a top perspective view of the system with the case cap removed showing section lines 9b-9b.

FIG. 9b is a side cross sectional view of the system as seen through section lines 9b-9b of FIG. 9a.

FIG. 10a is a top perspective view of the system with the case cap removed showing section lines 10b-10b.

FIG. 10b is a side cross sectional view of the system as seen through section lines 10b-10b of FIG. 10a.

FIG. 11a is a top perspective view of the system with the case cap removed showing section lines 11b-11b.

FIG. 11b is a side cross sectional view of the system as seen through section lines 11b-11b of FIG. 11a.

DETAILED DESCRIPTION

Figure 1:
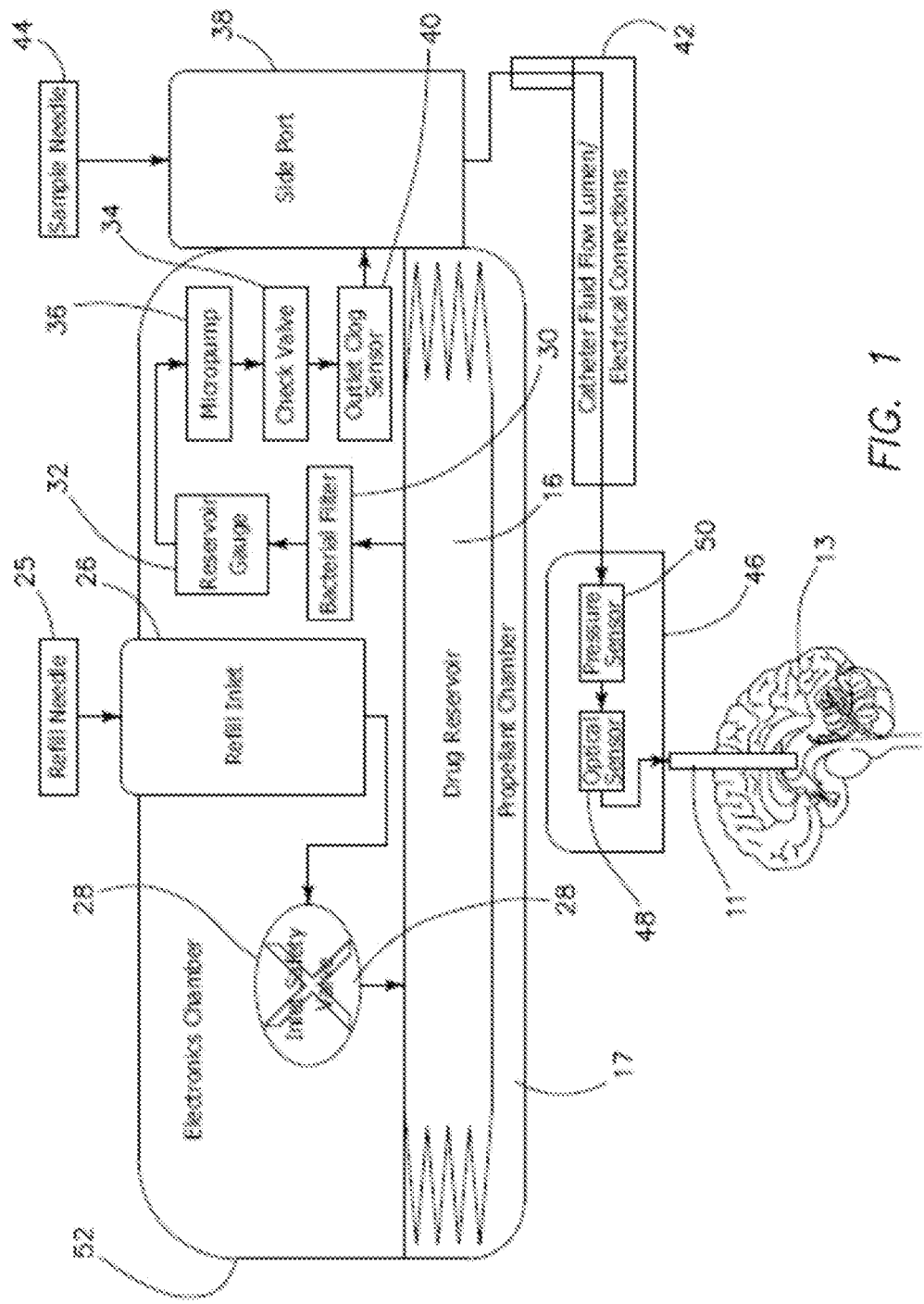
FIG. 1 is a diagram of the pump components with the arrows showing the direction of the fluid flow to brain via a ventriculoperitoneal (VP) shunt.

A system 10 of the first illustrated embodiment of the invention relates to medical apparatus containing a valve 12, a micropump 36, and a reservoir 16. The apparatus includes means 18 for regulating, controlling, and modulating a combination therapy of cytokine and chemotherapeutic agents for the purpose of tumor elimination. Biotherapy and combination therapy, using medicating agents such as, for example, biological response modifiers (BRMs) as agents or approaches, modifies the relationship between tumor and host, hence modifying the host's biologic response to tumor cells and chemotherapeutic agents. This combination therapy method has shown improved therapeutic indices. Hence, treatment of tumors with the use of BRMs and chemotherapy is copasetic with the principal goal where the patient must first achieve a complete response.

The approach of using combination therapies with the intent of increasing response rate due to synergetic effects of BRMs, due to their redundant and pleiotropic nature (combinations of cytokines with chemotherapy) provides improved treatment of the tumor. A variety of combinations of BRMs. (such as different Interferon INF (alpha., beta. gamma.) and of Interleukins (IL-2) or tumor necrosis factor (TNF) with IFN or IL-2 are some of the varieties of combinations in question) improve the results of tumor elimination. IL-2 appears to act primarily as an immuno-modulator whereas IFN has anti-proliferate effects. The use of BRMs and chemotherapy in combination of biotherapy is based on the rationale that the interaction of cytokines and cytotoxic drugs may occur on several levels, different mechanisms of actions; attacking the tumor, by modulating the pharmacokinetics of the chemotherapeutic agents as key enzymes (irrigation of solid tumor), attenuation of drug resistance mechanisms, modifications in permeability of the vascular system which allow increased accumulation of chemotherapeutic drugs at the tumor site, and reduction of tumor burden. The use of one modality to improve anti-tumor response increases production of cytokines, decreasing suppressor mechanisms. Other modalities are the patient's tolerance to cytotoxic effects, changing membrane characteristics of tumor cells (making it more susceptible to killing by chemotherapeutic agents) and decreasing the ability of tumor cell to metastasize.

The biomodulation action of the present system 10 is described as manipulating the metabolic pathway of a cytotoxic drug to increase the efficacy of selective protection of normal tissue. The target of modulations includes specific enzymes of drug metabolism, receptors for adhesion or growth, cell cycle phases, gene expression and immune system. In one embodiment, proper dosing and scheduling are used to obtain benefits in a combination of chemotherapy with biotherapy. The apparatus can be used for combination therapy such as IFN-C. with 5-FU (5-fluorouracil) and chemotherapy paired with IL-2 and IFN-C. in improving the effectiveness of tumor elimination.

The impact and efficacy of tumor treatment using BRMs and chemotherapy often requires that specific intricacies of physiologic and pharmacologic parameters be thoroughly measured. This complete evaluation measures not only the agent's effectiveness, but also considers cellular immune response. The steps for identification, isolation, recombinant expression and the physiological role as defined by the therapeutic model, are set by defining the pharmacokinetic as well as pharmacodynamic of the combination therapy.

The underlying hypothesis of cytotoxic drug is that more is better. Thus, a critical first step in administrating a cytotoxic agent is to determine the maximum tolerated dose (MTD). Clinical trials of BRM's demonstrated that immunologic effects occur at doses lower than the identified maximum tolerated dose (MTD). This phenomenon led to the concept of optimal biological dose (OBD). The hypothesis and the clinical facts lead to determine that OBD is that which, with a minimum of side effects, produces the improved desired response for the parameters deemed important with respect to a particular biological agent.

Biological response modifiers, BRMs, unlike drugs, have preprogrammed mechanisms and receptors available for them, which account for the difference between maximum tolerated doses (MTD) and optimal biological dose (OBD). Whereas cytotoxic agents possess the ability to maximize direct antitumor effects, BRMs are both cytotoxic and pleiotropic and have indirect immune cascades that mediate the tumor physiology and maximizes the tumor response.

The above hypothesis and clinical observations show the desirability of administration cycle of BRMs and chemotherapeutic agents on scale and measure which does not lend itself to the traditional approach of maximum tolerated dose. Hence, the ability to regulate and schedule the dose of the BRMs and/or chemotherapy is essential and is addressed by this system 10.

The disclosed system 10 and method 20 yield a better correlation between BRMs using cytokines such as interferon (IFN), interleukins (IL), hematopoietic factors (HGF), monoclonal antibodies (MAB), and tumor necrosis factor (TNF) in combination therapy with chemotherapeutic agents in achieving the desired goal of complete response.

The approach disclosed, using biotherapy with chemotherapy as treatment modality for cancer is not viewed as independent factors, but instead as an element of complex, intricate network producing a distinct response in overlapping effects. BRMs possess the phenomenon of pleiotropic effects, a single stimulus can induce a response from multiple cytokines including stimulating production of other agents, modulating receptor sites, and enhancing or inhibiting the biological activity of other cytokines. No therapy on its own (such as Interferon-alpha, -beta, -gamma. TNF-alpha, -beta, -gamma, angiogenetic drugs, anti-sense therapy, interleukins 1-12, hematopoietic growth factors, monoclonal antibodies and the variety of chemotherapeutic agents), has generated the "magic bullet" for curing cancer. A new rational approach which combines the known characteristics of tumor physiology and the cascades of biological response modifiers including BRMs optimal biological dose (OBD) as well as chemotherapeutic maximum tolerated dose (MTD) is used as clinical observation indicators.

Since BRMs cascade effects are somewhat known to those familiar with the art, and chemotherapeutic effects of cell deaths are preprogrammed events, the use of the apparatus and its associated circuitry of system 10 will enhance and/or modulate a variety of tumor growth factors and will enable a combination therapy to take place on the tumor site without the known side effects due to maximum dose of toxins. The ability of the apparatus of system 10 to change its preprogrammed sequence of events such as the release of various agents on a specific schedule and dose is due to the innate capability of the apparatus of system 10 to receive commands via its communication links. This allows a treatment change in mid-stream by transmitting program codes, which instruct a microcontroller 22 to enhance one process or another. The ability of the apparatus of system 10 to modulate and enhance tumor cells death is the mainstay of the technology disclosed.

The chemo immunotherapy model, by using the disclosed apparatus of system 10, allows the clinician to perform a selective treatment by preprogramming the targeted results. A typical example cited by clinical observation is Interferon C. and 5-fluorouracil and calcium leucovorin combination of dacarbazine, BCNU, cisplatin, and tamoxifen, followed by interferon C. and IL-2.

The above are examples of some of the approaches that can be used by a clinician in treating a tumor. In one embodiment, a multi-chamber pouch-type architecture diagrammatically shown in FIG. 1 with a preprogrammed instruction set allows the timed release of the agents discussed above. An "electrostatic muscle" enables the clinician to interfere and reduce or increase/change the medicating agent release based on tumor specific behavior, using known techniques of verification such as fluoroscopic and thermographic imagery to measure the success of the procedure by indicating reduction of tumor burden and tumor size, is the mainstay of the system 10 and its embodiments.

In one embodiment, the apparatus of system 10 can monitor and report to the clinician a set of biometric measures such as the temperature and the pH level at the tumor site, as well as the pressure of the tumor surrounding tissue. These are biometric measures and indications of the behavior of the tumor and its treatment history and give the clinician an added insight on the progress of the treatment and the response of the tumor to the treatment. This is due to the pronounced changes of these biometric indications in the vicinity of the tumor as a result of its biological activity, its response to medication, and its on-going growth or decay. For example, in the case of pH measurement, it is known that the extracellular pH of solid tumors is acidic. This acidic pH can have many consequences which are germane to the etiopathogenesis of cancer. Low pH causes tumorigenic transformation of primary Syrian hamster embryo cells. It is also known that low pH causes chromosomal rearrangements in Chinese hamster embryo cells. Low pH also induces immediate early gene expression and activates the proto-oncogene RAS, in kidney renal tubule. Low pH also increases in vitro migration and invasion. Culturing cells in a low pH environment causes them to be more metastic in vivo. Low pH also induces the expression of platelet derived endothelial cell growth in tumors in vivo. It is also known that low pH enhances resistance to weakly basic chemotherapeutic drugs.

Tumor cells generally metabolize lipids and glucose different from their normal counterparts and these have significant sequelae that are germane to the transformed phenotype. For example, tumors maintain elevated levels of phosphomonoesters, which are precursors to the metabolism of phospholipids. These are related to the tumorigenicity, and proliferation in a complex way and are markers for therapeutic effectiveness. Low extracellular pH can also promote a more aggressive tumor phenotype. A low interstitial pH is exacerbated by the fact that the tumor vasculature is inefficient. This inefficient vasculature also causes significant hypoxia, which contributes to the resistance of tumors to radiotherapy. The intercellular pH of cells in tumors is neutral-to-alkaline, which is used for continued cell proliferation.

Additional biometric measurements are available from pressure and temperature sensors embedded inside the apparatus of system 10. A major problem with conventional cancer therapy, such as radiotherapy and chemotherapy, is the lack of specificity of the cancer cell, except in the case of tumor tissue where high interstitial fluid pressure and elevated temperatures are shown to exist in tumor tissue as compared with those of a normal tissue. A step pressure gradient typically exists at the periphery of the tumor. Information relating to pressure gradient and temperature between the tumor site and the apparatus of system 10 can assist the clinician in evaluating the treatment history and its progress. For example, it is known that chemical and blood vessel activity in both pre-cancerous tissue and the area surrounding a developing breast cancer is almost always higher than in normal breast tissue. In an ever-increasing need for nutrients, cancerous tumors increase circulation to their cells by opening existing blood vessels and creating new ones (neoangiogenesis). This process frequently results in an increase in regional surface temperatures of the breast. These temperature variations may be among the earliest signs of breast cancer and/or a pre-cancerous state of the breast. Hence the incorporation of a temperature sensor 24 to allow the monitoring of temperature variations in correlation with treatment history provides the clinician with a set of valuable information relating to the progress in treating the tumor.

Cancerous cells generate more heat than healthy cells, due to hypervascularity or greater blood flow to the area, so tumors tend to be "hotter when viewed using methods such as thermotherapy. Breast thermograms are related to growth rate of breast carcinoma, and thermography can be used as a preliminary screening procedure.

Angiogenesis pertains to the development of blood vessels or blood supply and plays a role in the validity of thermo therapy. A tumor cannot grow bigger than a pinhead unless it establishes an independent blood supply. Certain types of vascular formations often precede the appearance of breast tumors on mammography, sometimes by more than a decade, but seem to go undetected or are considered normal asymmetry. When cancer is present, blood flow increases to the afflicted area and thus thermotherapy allows the clinician to find potential problem areas years before they become irreversible.

In one embodiment, the apparatus of system 10 described herein uses the fact that a tumor is generally hotter than its surroundings, a fact that makes the use of the disclosed device able to detect the tumor and chart the progress in its destruction. That is, as the tumor is destroyed its temperature is gradually reduced, until it reaches the temperature of the surroundings.

It is the goal of the disclosed apparatus of system 10 to eliminate the tumor and to be able to continuously monitor the progress in its treatment. The system disclosed enables the clinician to administer the BRMs and chemotherapeutic agents on schedule as well as duration and sequence preprogrammed to meet clinical observations with the intended goal of meeting complete response.

FIG. 1 shows the pump components with the arrows showing the direction of the fluid flow. As the medication is filled via the refill Inlet 26 through a first septum 25, the inlet safety valve 28 regulates and prevents over pressurization exerted by the refill syringe. Inlet safety valve 28 locks out when the refilling, handheld syringe (not shown) is pushed down. As the drug reservoir 16 is at negative pressure relative to the atmosphere, the medication in the refill syringe is automatically sucked in by the drug reservoir 16, which is shown as a bellows reservoir. The drug reservoir 16 is surrounded by a propellant liquid/gas mixture in propellant chamber 17 that maintains the reservoir pressure and compensates for the loss of medication due to pumping. As the medication is refilled, the propellant transitions from gas to liquid. An optional bacteria filter 30 sits between the reservoir 16 and reservoir gauge pressure sensor 32 that senses the pressure in the reservoir 16. This pressure is correlated with the reservoir volume due to the spring loading of the resilient bellows shape of reservoir 16. The passive check valve 34 ensures the liquid flows in only one direction and prevents back flow into the reservoir 16. The piezo micropump 36 actuates the liquid flow out of the reservoir 16 into the side port 38. The outlet clog sensor 40 is another pressure sensor that detects pressure spikes in the liquid flow to sense any clogging in the side port 38 and catheter 42. The side port 38 contains a second septum 44 with a smaller diameter opening for a smaller needle. This needle can be used to unclog the catheter 42 by flushing or withdraw patient fluid for laboratory testing. The catheter 42 is a dual lumen catheter-one lumen for medication liquid and the other for electrical wires going to the shunt sensor 46, which contains an optical sensor 48 and a third pressure sensor 50 for cranial pressure sensing.

Figure 2:
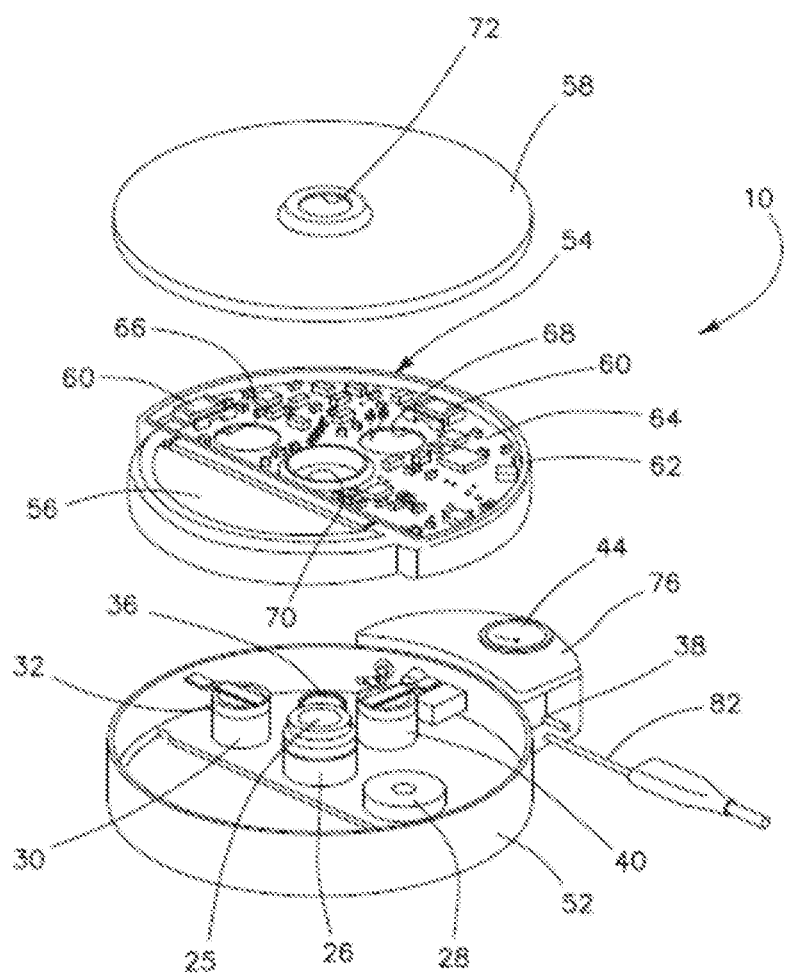
FIG. 2 is a perspective exploded view of the pump interior. The electronics and battery are hermetically sealed from the fluid chamber below the fluidic plate.

FIG. 2 is an exploded perspective view of various components in system 10 which comprise and is sometimes referred to collectively as the implantable pump, some of which components are described in connection with FIG. 1 above. All components are made of either medical grade titanium or silicone in order to be MRI compatible. The titanium components are laser welded to fluidic plate 74 of case 52 to create a hermetic seal with case 52. The hermetic seal protects the electrical components 54 and battery 56 from corrosion.

Mid layer 62 carries battery 56 and all the electronic and electrical components 54 in a sealed electronics chamber 64. Sealing through holes 66, 68 and 70 are defined in the floor of electronics chamber 64 of mid layer 62 to allow pressure sensor 32 to be disposed through hole 66 and connected to terminal 60 in electronics 54. Sealing hole 68 is similarly provided to allow the assembly of piezo micropump 36, check valve 34 and outlet clog sensor 40 to be disposed therethrough and coupled to connector 60. Refill inlet 26 is disposed through sealing hole 70 to allow access to refill inlet 26 through first septum 25. A cap 58 closes and seals with case body 52 thereby providing electronics chamber 64 with a hermetically sealed containment. Cap 58 has a central sealing hole 72 defined therein to allow refill inlet 26 to extend above cap 58.

Figure 2A:
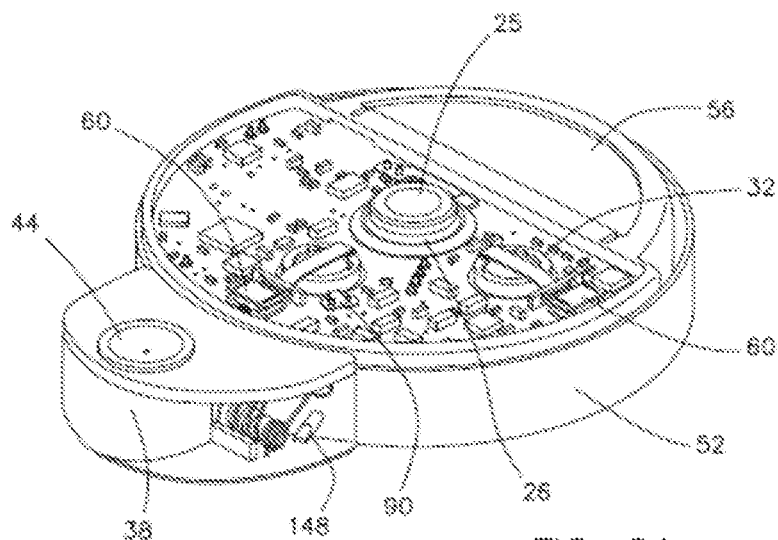
FIG. 2a is a top perspective view of the pump system of FIG. 2 shown with the cover and side port side wall removed.

FIG. 2a is a top perspective view of the pump system of FIG. 2 shown with the cover and side port side wall removed. Refill inlet 62 is shown entending through sealing through hole 70 and ultimately through the case cap 58 that will be placed thereover. Pressure sensor 32 is shown extending through sealing hole 66 and electrically coupled to a terminal 60. Similarly, outlet clog sensor 40 is shown extending through sealing hole 68 and electrically coupled to a terminal 60.

Figure 3:
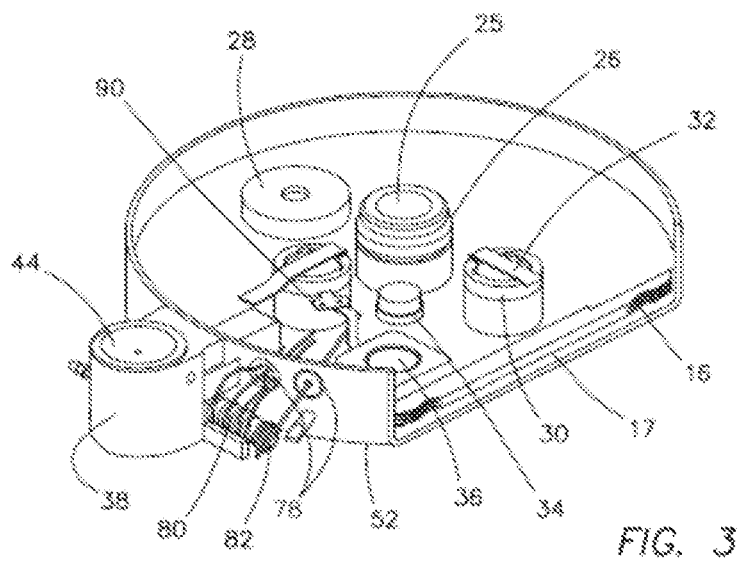
FIG. 3 is a cut-away perspective view of the pump components that are laser welded to the fluid plate. The cut away section shows the drug reservoir bellow inside the propellant chamber. The electrical feedthroughs are laser welded to the outer can to provide a hermetical seal.

FIG. 3 shows the cut-away section of the drug reservoir bellow 16 under the fluidic plate 74 on which all fluidic components are laser welded. The silicone cover 76 on the side port 38 in FIG. 2 is removed in FIG. 3 to show the components under cover 76. Laser welded electrical feedthroughs 78 are used to bring the signals out to the side port 38 and provide a hermetic seal. Bluetooth antenna 80 is housed inside the side port 38 and connected to electronics in chamber 64 through feedthroughs 78. Interlaced electrical and insulation rings are used to connect to the wiring 82 in the catheter 42.

Figure 8:
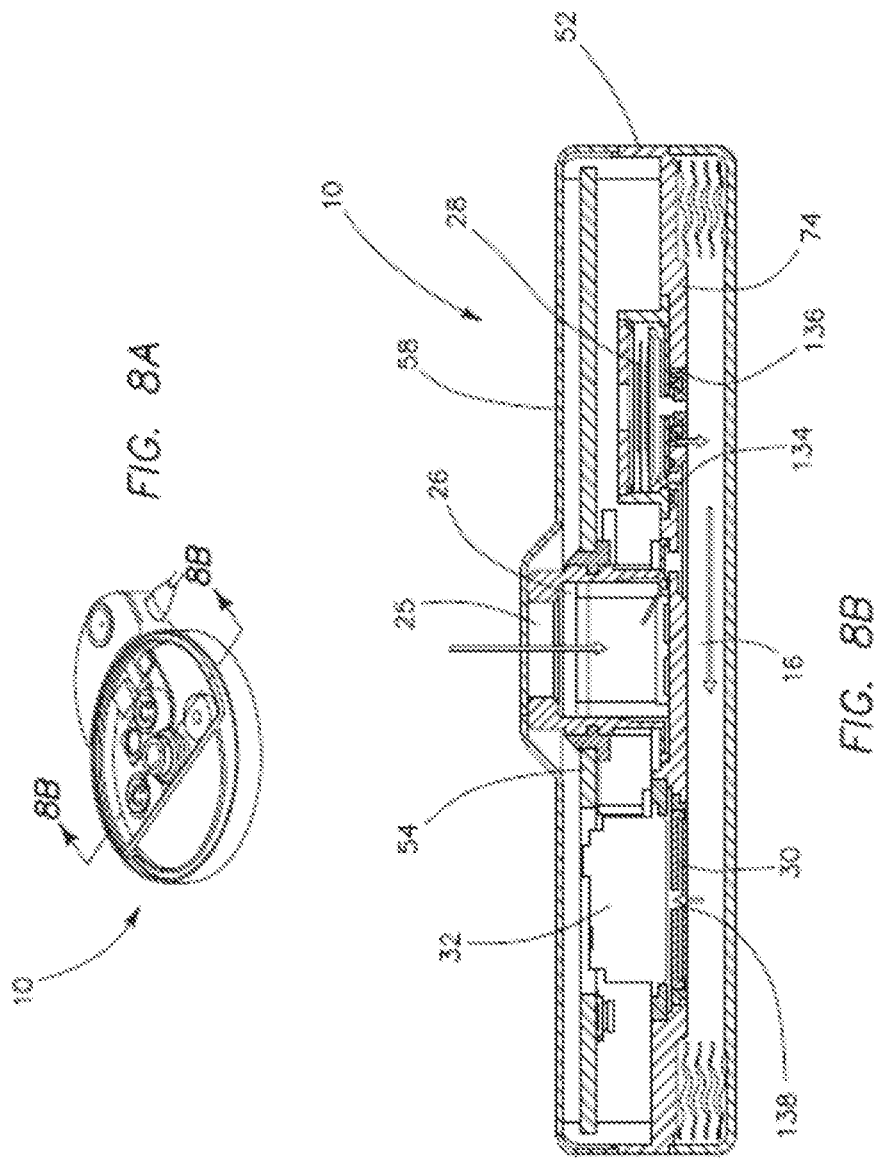

FIG. 8a is a top perspective view of the system 10 with the case cap 58 removed showing section lines 8b-8b. FIG. 8b is a side cross sectional view of the system 10 as seen through section lines 8b-8b of FIG. 8a. FIG. 8b shows the fluid path as it enters through septum 25 into refill inlet 26. The fluidic plate 74 includes fluid channels defined therein that guide the fluid flow. The fluid flows through inlet channel 134 to the inlet safety valve 28 before flowing into the reservoir 16 through reservoir channel 136. The fluid exits the reservoir 16 via the bacteria filter 30 through filter channel 138 into the reservoir gauge 32.

Figure 9:
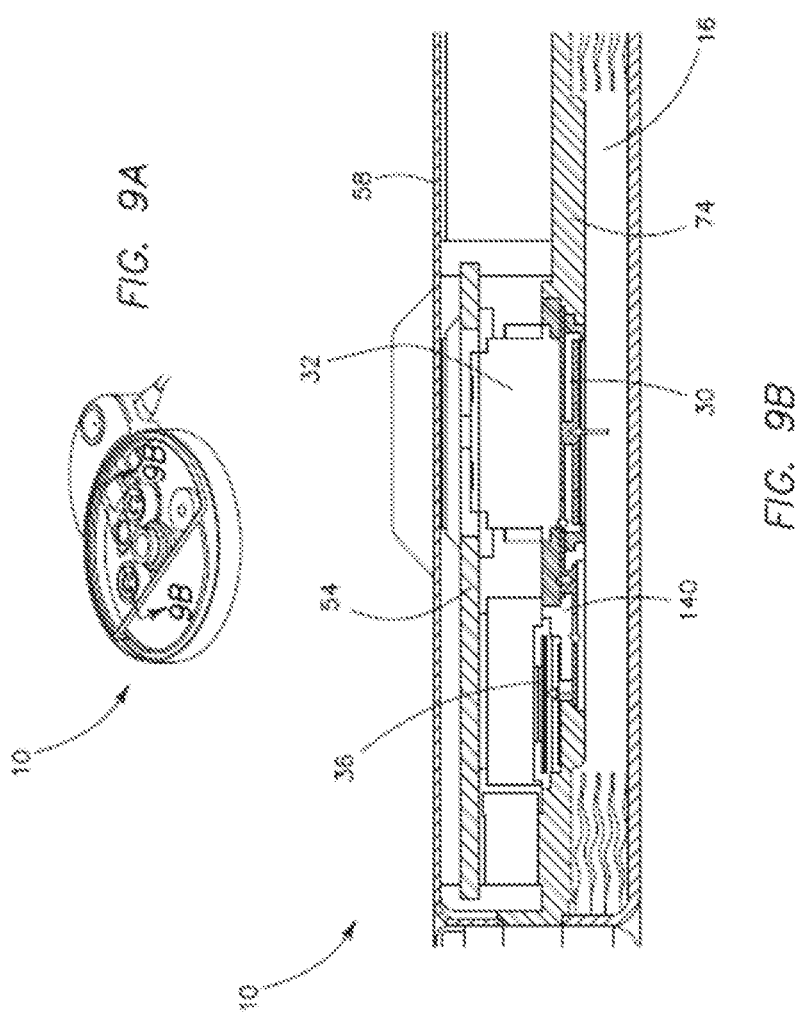

FIG. 9a is a top perspective view of the system with the case cap removed showing section lines 9b-9b. FIG. 9b is a side cross sectional view of the system as seen through section lines 9b-9b of FIG. 9a. FIG. 9b shows the flow path from inlet pressure sensor or reservoir gauge sensor 32 through micropump channel 140 to micropump 36.

Figure 10:
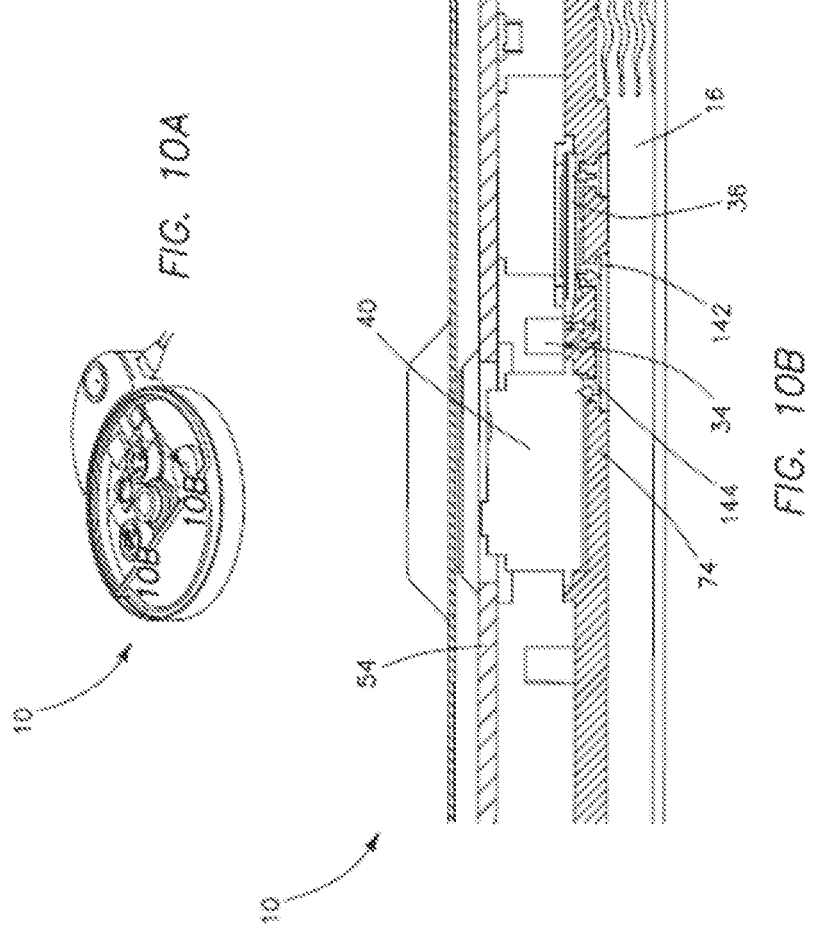

FIG. 10a is a top perspective view of the system with the case cap removed showing section lines 10b-10b. FIG. 10b is a side cross sectional view of the system as seen through section lines 10b-10b of FIG. 10a. FIG. 10b illustrates the fluid flow from micropump 36 through check valve channel 142 to check valve 34. The flow then continues forward, if at all, through outlet clog sensor channel 144 to outlet clog sensor 40.

Figure 11:
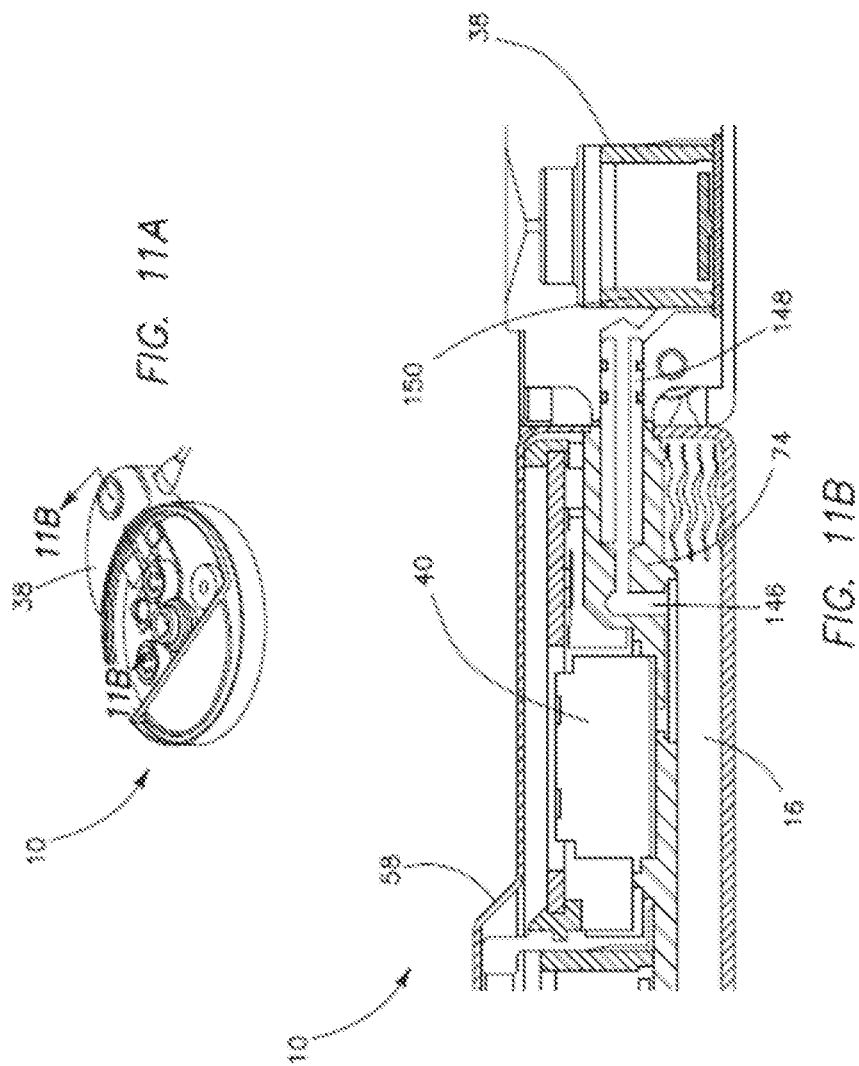

FIG. 11a is a top perspective view of the system with the case cap removed showing section lines 11b-11b. FIG. 11b is a side cross sectional view of the system as seen through section lines 11b-11b of FIG. 11a. Flow of fluid is shown from outlet clog sensor 40 through side port channel 146 to fluid outlet 148 through coarse filter 150 and into side port 38 from whence it is communicated to catheter 42.

Figure 7:
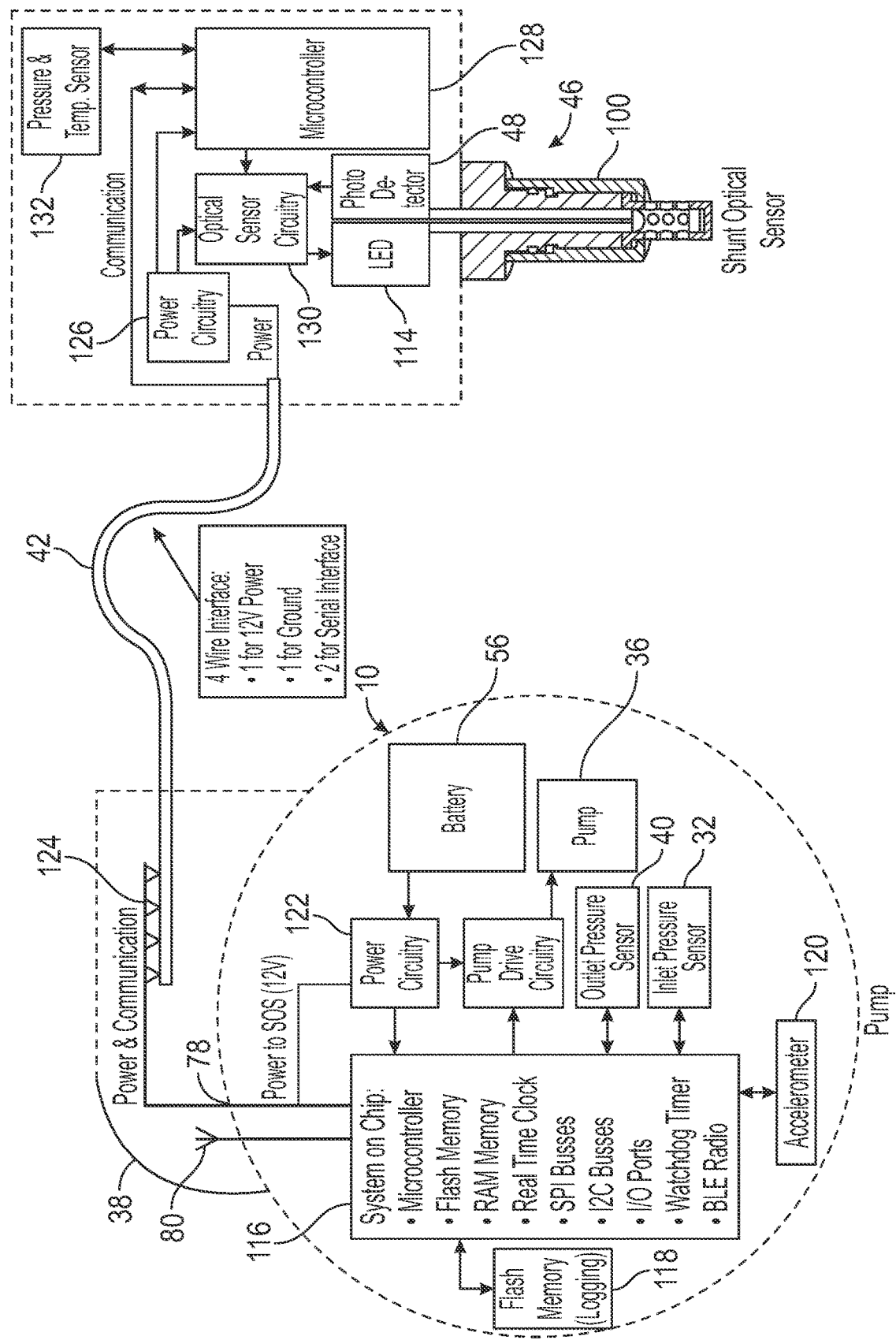
FIG. 7 is a block diagram of the electronic components in the pump system and in the VP shunt.

FIG. 7 is a simplified block diagram of the circuitry in system 10 and VP shunt 46. System on a chip 50 includes a large scale integrated circuit that includes a microcontroller, a flash memory, a random access (RAM) memory, a real time clock, serial peripheral interface (SPI) busses, inter-integrated circuit (I2C) busses, input/output ports, a watchdog timer and a Bluetooth low energy (BLE) radio. Coupled to chip 50 and serving as peripheral circuits are a flash memory 52 for logging, an accelerometer 54, inlet pressure sensor or reservoir gauge 32, outlet pressure sensor or outlet clog sensor 40, and power circuitry 122. Electrical connection to catheter 42 is made in side port 38 by means of electrical connector 124.

VP shunt 46 is powered by battery 56 through catheter 42 and is conditioned by VP power circuitry 126. Power is also directly supplied to VP microcontroller 128, which controls circuit operation in VP shunt 46 by controlling optical sensor circuitry 130. LED source 114 and photodetector 48 are coupled to optical sensor circuitry 130. Additional pressure and temperature sensors 132 are also coupled to microcontroller 128 for monitoring conditions in the environment of VP shunt catheter 100.

Figure 4:
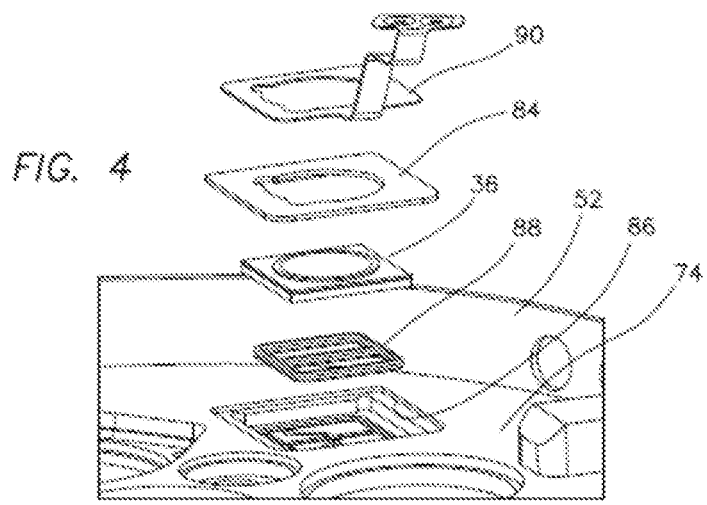
FIG. 4 is a partial perspective exploded view of the piezo pump mechanism components that are hermetically sealed by being laser welded to the fluid plate.

FIG. 4 shows how the piezo micropump 36 is hermetically sealed to the fluidic plate 74. Silicon based piezo micropump 36 is hermetically bonded to the titanium hermetic mount cap 84, which is laser welded to the fluidic plate 74. Piezo micropump 36 is mounted in a cavity 86 defined into plate 74. Cavity 86 contains fluidic channels that the micropump 36 uses to pump the medication. The outlet channel from cavity 86 leads to the check valve 34. Micropump 36 is bedded and sealed in cavity 86 by means of shaped silicone seal 88. Micropump 36 is wire bonded to flexible electrical cable 90, which in turn is wire bonded to electronic components 54.

Figure 5A:
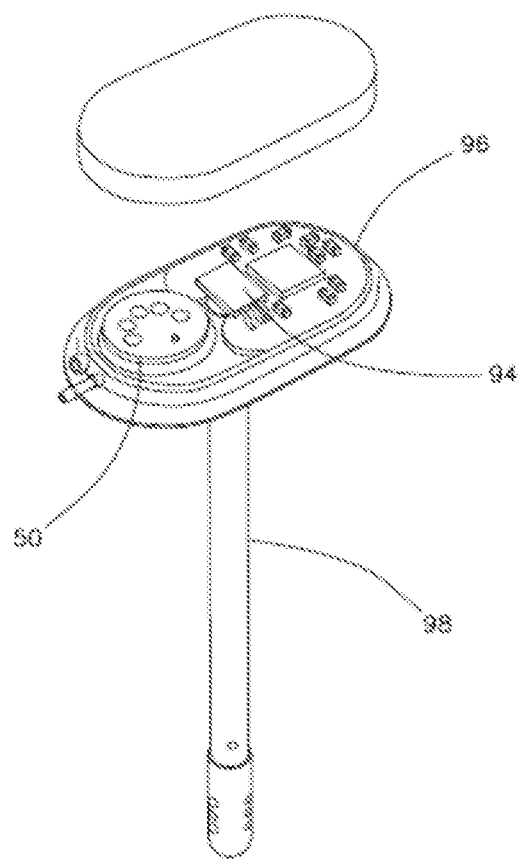
FIG. 5a is a photographic exploded perspective view of a ventriculoperitoneal (VP) shunt with optical and pressure sensors.
Figure 5B:
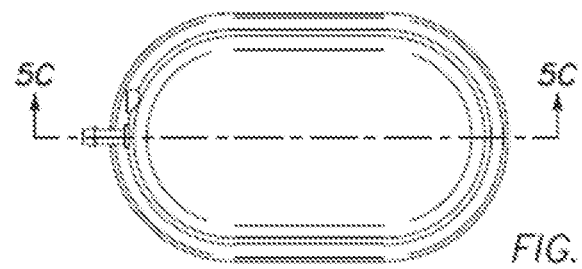
FIG. 5b is a top plan view of the shunt of FIG. 5a in a first azimuthal orientation parallel with the page.
Figure 5C:
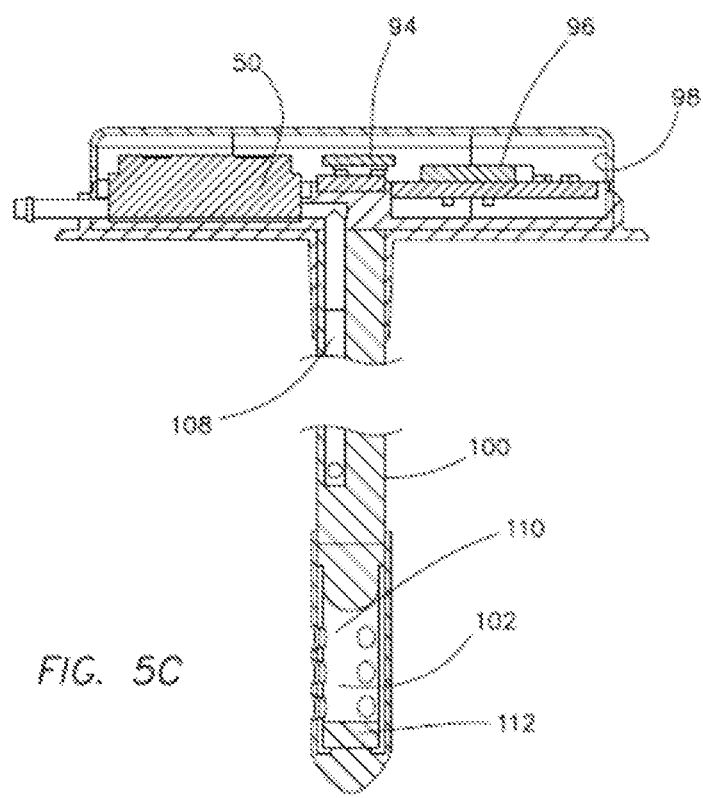
FIG. 5c is a side cross sectional view of the shunt of FIG. 5a as seen through section lines A-A of FIG. 5b.

FIGS. 5a-5e show the VP shunt 11 with its optical and pressure sensors. Shunt 11 is a skull mounted Ommaya shunt as disclosed in greater detail in PCT Patent Application, PCT/US17/32570, designating the United States and incorporated herein by reference in its entirety. The electronics 96 are enclosed in a hermetic chamber 58 best seen in FIG. 5c and includes a microprocessor, memory as part of electronics 96, and LED and photodiode detector control circuits 94. The shunt 11 connects with a catheter 42 communicated the pump system 10. There are electrical connections included in catheter 42 for power, ground, and signal lines to the pump system 10 with shunt 11. The medication received through catheter 42 is directed down into the intraventricular catheter 100 that contains a fluid lumen 108 and two optical fibers 104, 106 as best seen in FIG. 5e. LED's 114 of different wavelengths, a calibration detector and a photodiode detector or optical sensor 48 are mounted in the hermetic chamber 98 as best seen in FIG. 5e. Light from the LED's 114 is coupled into a fiber-optic 104 which is hermetically mounted to the chamber 98. Light is conducted by the fiber-optic 104 and exits through the fiber face into a chamber 110 in the catheter tip 102 open to cerebral spinal fluid (CSF). At the catheter tip 102, the light is reflected through the CSF chamber 110 by a 90° mirror 112 into a second fiber-optic 106. Light is conducted through the second fiber-optic 106 and is emitted through the fiber face back into the hermetic chamber 98 onto a photodiode detector 48.

As MTX CSF concentration increases, light absorption increases, and the concentration can be calculated from the photodiode detector reading. The concentration of MTX in CSF is measured at a sampling rate adequate to control drug delivery to maintain concentration within the therapeutic range. The closed loop control algorithm is programmed into the pump memory included in electronics 54. If MTX CSF concentration exceeds the upper limit or falls below a lower limit, a high MTX CSF or low MTX CSF concentration alarm is tripped in the pump system 10 and the clinician will be immediately notified. In addition to the optical sensor (not shown), the shunt 11 has a pressure sensor 50 that monitors intracranial pressure (ICP) and detects if there is a fluid leak between the pump system 10 and the shunt 11. If a leak is detected an alarm is tripped. If ICP exceeds a clinician set upper limit, a high ICP pressure alarm is tripped.

Figure 12:
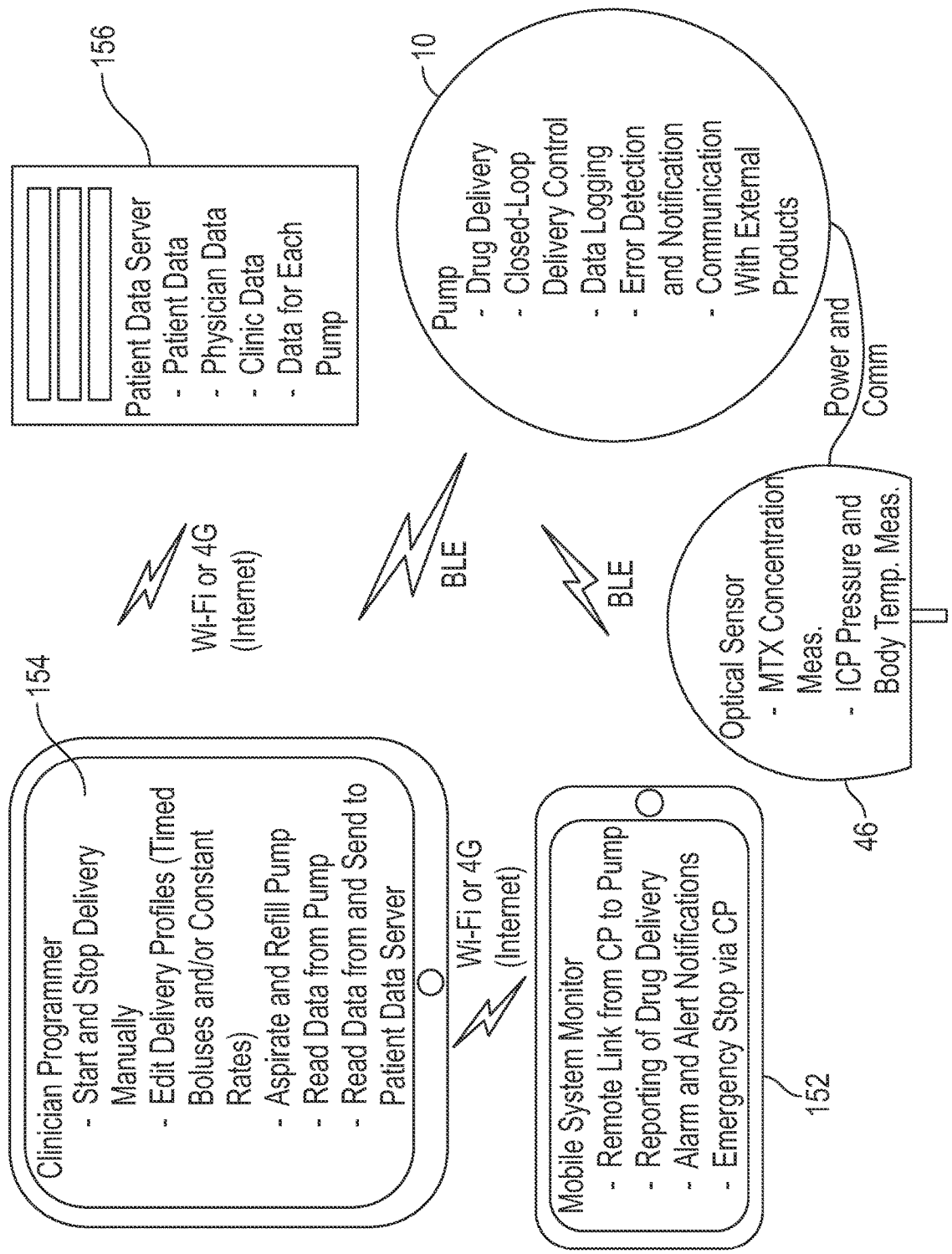
FIG. 12 is a diagram illustrating the software control of system 10 in combination with VP shunt 46.

FIG. 12 is a diagram illustrating the software control of system 10 in combination with VP shunt 46. System 10 and VP shunt 46 intercommunicates or interacts through BLE wireless communications a mobile system monitor 152 carried separately by the patient, a clinician programmer 154 at the clinic and a patient data server 156 that records all data and events. Mobile system monitor 152 and clinician programmer 154 are conventional programmable mobile telephones or tablets blue tooth communicated with system 10, VP shunt 46 and patient data server 156 via conventional WiFi or cellular telephone communication channels. VP shunt 46 measures drug concentrations, e.g. MTX drugs, intracranial blood pressure and body temperature. These parameters are communicated to system 10 and hence to mobile system monitor 152, clinician programmer 154 and/or patient data server 156. Pump system 10 regulates drug delivery through a closed loop control, performs data logging, error detection and notification of the same, and BLE communications. Clinician programmer 154 allows for manual starting and stopping of drug delivery, edits delivery profiles for timed or constant drug boluses, is used to aspirate and fill pump system 10, reads data from system 10 and bidirectionally communicates data with patient data server 156. Mobile system monitor 152 functions as a remoted link between clinician programmer 154 and pump system 10. It reports drug delivery by system 10, manages alarms and notifications, and incorporates an emergency stop with the clinician programmer 154. Patient data server 156 provides an accessible data storage for patient data, physician data, clinic data, and a historical record for each pump system 10.

Figure 6:
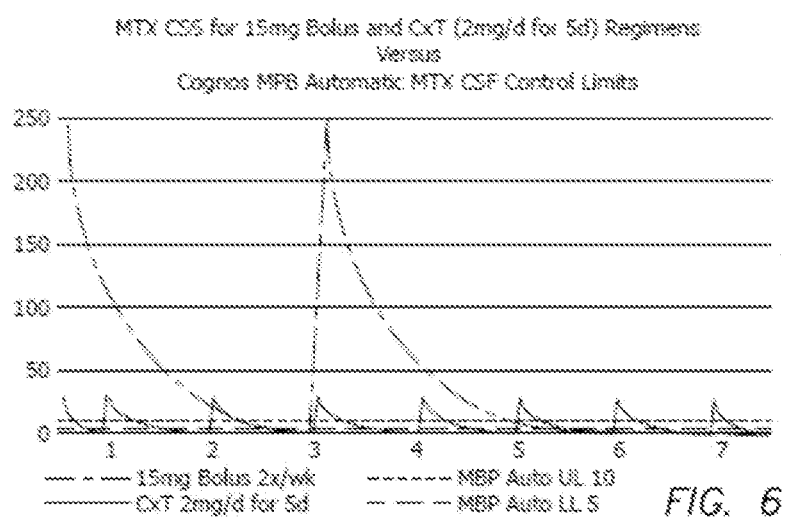
FIG. 6 is a graph of drug concentrations in the CSF verses time in days of a delivered cancer drug MTX comparing conventional deliveries of 15 mg twice per week to metronomic deliveries of the drug at 2 mg per day for seven days using the pump of the illustrated embodiments.

FIG. 6 is a graph of drug concentrations in the brain verses time, which illustrates the metronomic delivery of a cancer drug MTX into the CSF compared with periodic bolus injection. The median MTX CSF concentration for one week of the induction phase for the bolus regimen is compared with the CxT regimen and potential control bands. MTX CSF pharmacokinetics vary widely among patients, and automatic control of MTX CSF concentration eliminates this complicating variable enabling physicians to focus more on treatment outcomes. Toxicity complication rates can be significantly reduced. Efficacy may be improved by continuously maintaining MTX CSF concentration within the therapeutic range and below toxicity limits. Further, patients will only need to visit with their physician for monitoring treatment progression every two weeks during induction phase, and once a month during consolidation and maintenance phases. This will free the patients to spend far more of their remaining time in normal life activities.

The illustrated embodiments of the invention can now be summarized as follows. One embodiment is an MRI compatible apparatus including: a refillable drug reservoir; a hermetically sealed, implantable chamber; a pump disposed in and hermetically sealed within the hermetically sealed, implantable chamber and fluidically communicated to the drug reservoir; and control electronics disposed in and hermetically sealed within the hermetically sealed, implantable chamber and electrically communicated to the pump. The refillable drug reservoir, hermetically sealed, implantable chamber, pump and control electronics are MRI compatible.

The apparatus further includes a bacterial filter disposed in and hermetically sealed within the MRI compatible, hermetically sealed, implantable chamber and fluidically communicated between the drug reservoir and the pump.

The apparatus further includes an MRI compatible inlet safety valve disposed in and hermetically sealed within the MRI compatible, hermetically sealed, implantable chamber and fluidically communicated between the drug reservoir and the refill inlet.

Drug reservoir is bellows shaped and resilient, and the apparatus further includes an MRI compatible reservoir gauge pressure sensor to sense pressure in the drug reservoir, which pressure is correlated with the drug reservoir's volume due to spring loading of the bellows shape of the drug reservoir.

The apparatus further includes a catheter or VP shunt, and an MRI compatible outlet clog sensor to detect a pressure spike in liquid flow to sense clogging in the catheter or VP shunt.

The MRI compatible refillable drug reservoir is hermetically sealed within the MRI compatible, hermetically sealed, implantable chamber.

The VP shunt comprises an optical source and detector to monitor the concentration of medicating agents dispensed from the drug reservoir.

The pump is remotely programmable to adjust the delivery of medicating agents.

The control electronics comprises a microprocessor and memory programmable for dispensing medicating agents, and for controlling, regulating, and reporting of biological response parameters arising from the medicating agents.

The drug reservoir is selectively loaded with as biological response modifiers, enzymes, therapeutic agents, drugs, and chemotherapy agents.

The apparatus further includes a VP shunt and where a patient has a solid tumor, where the VP shunt is arranged to irrigate the solid tumor and where the drug reservoir is loaded with an agent to increase cell adhesion molecules targeting the solid tumor used for adherence of cytotoxic cells to the solid tumor.

The control electronics includes remotely programmable control circuitry with stored look-up-tables to selectively deliver an optimal biological dose (OBD) as opposed to a maximum tolerated dose (MTD).

The drug reservoir is loaded with a chemotherapeutic agent, where the control electronics includes remotely programmable control circuitry incorporating stored pharmacokinetic and pharmacodynamic parameters associated with the chemotherapeutic agent, and where the pump is controlled by the programmable control circuitry to deliver the chemotherapeutic agent in view of the incorporated pharmacokinetic and pharmacodynamic parameters to achieve a desired result without any toxic side effect.

The control electronics includes remotely programmable control circuitry to regulate dispensation of tumor BRMs according to their pleiotropic nature to allow for biological processes or mechanisms to develop by selectively reducing or enhancing selected agents in the drug reservoir to provide patient-specific treatment.

The control electronics includes remotely programmable control circuitry to dispense agents within a specific time domain to a tumor site to selectively provide an immune modulating effect and/or anti-proliferate effect, and dosing depending on which effect is to be maximally stimulated.

The control electronics includes remotely programmable control circuitry selectively controlling the pump to provide maximum dosing of a chemotherapeutic agent to a tumor site by using the maximum tolerated doses (MTD) in a time domain which does not interfere with the activity of BRMs.

The control electronics includes remotely programmable control circuitry to allow an expression of a BRMs cascade effect due to communication of cytokines as messengers with their synergistic, additive or antagonistic interactions that affect a target tumor cell.

The control electronics includes remotely programmable control circuitry to schedule delivery of medicating agents, including chemotherapy and BRMs, based on toxicity, measures of bioavailability, solubility, and concentration, and of circulation based on locality.

The control electronics includes remotely programmable control circuitry to selectively deliver agents in selective doses on a selective schedule based on individual differences of various tumors depending on the disease stage, immune factors, body weight, age and chronobiology.

The control electronics includes remotely programmable control circuitry to mitigate factors such as peak serum concentration associated with peak occurrence of side effects of an agent intravenously injected, so that the peak concentration of the agent is correlated clinically with a peak side effect.

The control electronics includes remotely programmable control circuitry to selectively deliver an agent having a bell-shaped response curve as concentration of the agent increases to provide improved control of the use of the agent according to the a bell-shaped response curve.

The control electronics includes remotely programmable control circuitry to provide an effective mode of administrating an agent in combination with chemotherapy by selectively scheduling delivery local administration of different agents in combination with monoclonal antibodies and tumor necrosis factors (TFNs).

The control electronics includes remotely programmable control circuitry to selectively control or exploit delivery, dose, cycle, circadian time effects and the entire pharmacokinetic and pharmacodynamic behavior of an agent and to provide corresponding feedback reports in terms of a biological measure of tumor responses to the agent.

The control electronics includes remotely programmable control circuitry to provide local administration of BRMs and chemotherapeutic agents to enhance mechanisms that support overlapping effects in reducing tumor burden and elimination of tumors, to induce an improved response by using biomodulators augmenting patient anti-tumor response via production of cytokines, to decrease suppressor mechanisms, to increase patient immunological response, to limit toxicity of an agent by locality of delivery, to maximize the dose, to increase susceptibility of a cell membrane characteristic for an improved chemotherapy result, or to decrease tumor metastasis.

The control electronics includes remotely programmable control circuitry use a Creech technique of regional or isolated limb perfusion to selectively delivery high-doses of chemotherapy to an isolated or local site of melanoma or sarcoma by using BRMs and TNF-α to damage neovascular circulation surrounding a tumor without destroying normal tissue.

The control electronics includes remotely programmable control circuitry to selectively deliver a plurality of agents using a corresponding selectively determined plurality of doses and a corresponding selectively determined plurality of schedules of the plurality of agents to maximize the anti-tumor effects of each agent while not increasing toxicity.

Considering the apparatus from another view, it includes: an MRI compatible refillable drug reservoir; an MRI compatible, hermetically sealed, implantable chamber; an MRI compatible refill inlet disposed in and hermetically sealed within the MRI compatible, hermetically sealed, implantable chamber and fluidically communicated to the drug reservoir; an MRI compatible pump disposed in and hermetically sealed within the MRI compatible, hermetically sealed, implantable chamber and fluidically communicated to the drug reservoir; MRI compatible control electronics disposed in and hermetically sealed within the MRI compatible, hermetically sealed, implantable chamber and electrically communicated to the pump; an MRI compatible catheter electrically communicated with the MRI compatible control electronics and fluidically communicated with the pump; and an MRI compatible ventriculoperitoneal (VP) shunt electrically and fluidically communicated with the catheter.

Still further, the illustrated embodiments include methods for operating the above apparatus as follows.

One embodiment is an MRI compatible method including the steps of: selectively filling a refillable drug reservoir disposed in a hermetically sealed, implantable chamber; selectively operating a pump disposed in and hermetically sealed within the hermetically sealed, implantable chamber and fluidically communicated to the drug reservoir; and operating and remotely programming control electronics disposed in and hermetically sealed within the hermetically sealed, implantable chamber and electrically communicated to the pump. The refillable drug reservoir, hermetically sealed, implantable chamber, pump and control electronics are MRI compatible.

The method further includes the step of employing a bacterial filter disposed in and hermetically sealed within the MRI compatible, hermetically sealed, implantable chamber and fluidically communicated between the drug reservoir and the pump.

The method further includes the step of employing an MRI compatible inlet safety valve disposed in and hermetically sealed within the MRI compatible, hermetically sealed, implantable chamber and fluidically communicated between the drug reservoir and the refill inlet.

The drug reservoir is bellows shaped and resilient, and the method further includes the step of employing an MRI compatible reservoir gauge pressure sensor to sense pressure in the drug reservoir, which pressure is correlated with the drug reservoir's volume due to spring loading of the bellows shape of the drug reservoir.

The method further includes a catheter or VP shunt, and an MRI compatible outlet clog sensor and includes the step of detecting a pressure spike in liquid flow to sense clogging in the catheter or VP shunt.

The method includes the step of hermetically sealing the MRI compatible refillable drug reservoir within the MRI compatible, hermetically sealed, implantable chamber.

The method includes the step of VP shunt deploying an optical source and detector to monitor the concentration of medicating agents dispensed from the drug reservoir.

The method includes the step of remotely programming the pump to adjust the delivery of medicating agents.

The control electronics comprises a microprocessor and memory programmable for dispensing medicating agents, and the method includes the steps of controlling, regulating, and reporting of biological response parameters arising from the medicating agents.

The method includes the step of selectively loading the drug reservoir with biological response modifiers, enzymes, therapeutic agents, drugs, and chemotherapy agents.

The method further includes locally disposing a VP shunt into a solid tumor, irrigating the solid tumor and with an agent to increase cell adhesion molecules targeting the solid tumor used for adherence of cytotoxic cells to the solid tumor.

The method includes the step of remotely programming control electronics with stored look-up-tables to selectively deliver an optimal biological dose (OBD) as opposed to a maximum tolerated dose (MTD).

The method includes the step of loading the drug reservoir with a chemotherapeutic agent, and remotely programming the control electronics to incorporate stored pharmacokinetic and pharmacodynamic parameters associated with the chemotherapeutic agent, and controlling the pump by the programmable control circuitry to deliver the chemotherapeutic agent in view of the incorporated pharmacokinetic and pharmacodynamic parameters to achieve a desired result without any toxic side effect.

The method includes the step of remotely programming the control electronics to regulate dispensation of tumor BRMs according to their pleiotropic nature to allow for biological processes or mechanisms to develop by selectively reducing or enhancing selected agents in the drug reservoir to provide patient-specific treatment.

The method includes the step of remotely programming the control electronics to dispense agents within a specific time domain to a tumor site to selectively provide an immune modulating effect and/or anti-proliferate effect, and dosing depending on which effect is to be maximally stimulated.

The method includes the step of remotely programming the control electronics to selectively control the pump to provide maximum dosing of a chemotherapeutic agent to a tumor site by using the maximum tolerated doses (MTD) in a time domain which does not interfere with the activity of BRMs.

The method includes the step of remotely programming the control electronics to allow an expression of a BRMs cascade effect due to communication of cytokines as messengers with their synergistic, additive or antagonistic interactions that affect a target tumor cell.

The method includes the step of remotely programming the control electronics to schedule delivery of medicating agents, including chemotherapy and BRMs, based on toxicity, measures of bioavailability, solubility, and concentration, and of circulation based on locality.

The method includes the step of remotely programming the control electronics to selectively deliver agents in selective doses on a selective schedule based on individual differences of various tumors depending on the disease stage, immune factors, body weight, age and chronobiology.

The method includes the step of remotely programming the control electronics to mitigate factors such as peak serum concentration associated with peak occurrence of side effects of an agent intravenously injected, so that the peak concentration of the agent is correlated clinically with a peak side effect.

The method includes the step of remotely programming the control electronics to selectively deliver an agent having a bell-shaped response curve as concentration of the agent increases to provide improved control of the use of the agent according to the a bell-shaped response curve.

The method includes the step of remotely programming the control electronics to provide an effective mode of administrating an agent in combination with chemotherapy by selectively scheduling delivery local administration of different agents in combination with monoclonal antibodies and tumor necrosis factors (TFNs).

The method includes the step of remotely programming the control electronics to selectively control or exploit delivery, dose, cycle, circadian time effects and the entire pharmacokinetic and pharmacodynamic behavior of an agent and to provide corresponding feedback reports in terms of a biological measure of tumor responses to the agent.

The method includes the step of remotely programming the control electronics to provide local administration of BRMs and chemotherapeutic agents to enhance mechanisms that support overlapping effects in reducing tumor burden and elimination of tumors, to induce an improved response by using biomodulators augmenting patient anti-tumor response via production of cytokines, to decrease suppressor mechanisms, to increase patient immunological response, to limit toxicity of an agent by locality of delivery, to maximize the dose, to increase susceptibility of a cell membrane characteristic for an improved chemotherapy result, or to decrease tumor metastasis.

The method includes the step of remotely programming the control electronics to use a Creech technique of regional or isolated limb perfusion to selectively delivery high-doses of chemotherapy to an isolated or local site of melanoma or sarcoma by using BRMs and TNF-$\alpha$ to damage neovascular circulation surrounding a tumor without destroying normal tissue.

The method includes the step of remotely programming the control electronics to selectively deliver a plurality of agents using a corresponding selectively determined plurality of doses and a corresponding selectively determined plurality of schedules of the plurality of agents to maximize the anti-tumor effects of each agent while not increasing toxicity.

Considering the method from another view, it includes the steps of: providing an MRI compatible refillable drug reservoir; providing an MRI compatible, hermetically sealed, implantable chamber; providing an MRI compatible refill inlet disposed in and hermetically sealed within the MRI compatible, hermetically sealed, implantable chamber and fluidically communicated to the drug reservoir; providing an MRI compatible pump disposed in and hermetically sealed within the MRI compatible, hermetically sealed, implantable chamber and fluidically communicated to the drug reservoir; providing MRI compatible control electronics disposed in and hermetically sealed within the MRI compatible, hermetically sealed, implantable chamber and electrically communicated to the pump; providing an MRI compatible catheter electrically communicated with the MRI compatible control electronics and fluidically communicated with the pump; and providing an MRI compatible ventriculoperitoneal (VP) shunt electrically and fluidically communicated with the catheter.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An magnetic resonance imaging (MRI) compatible apparatus comprising:
   a refillable drug reservoir;
   a hermetically sealed, implantable chamber defined between a fluidic plate and a cap;
   a pump hermetically sealed to the fluidic plate and fluidically communicated to the drug reservoir;
   control electronics coupled to a mid layer disposed within the hermetically sealed, implantable chamber, the control electronics electrically communicated to the pump; and a refill inlet, a pressure sensor, and an outlet clog sensor, where each of the refill inlet, the pressure sensor, and the outlet clog sensor are coupled to the fluidic plate,
where the mid layer comprises a plurality of holes defined therein, where each of the plurality of holes accommodate a respective one of the refill inlet, the pressure sensor, and the outlet clog sensor,
where the pressure sensor and the outlet clog sensor are electrically communicated to the control electronics coupled to the mid layer, and
where the refillable drug reservoir, the hermetically sealed, implantable chamber, the pump and the control electronics are MRI compatible.

2. The apparatus of claim 1 further comprising a bacterial filter disposed in and hermetically sealed within the MRI compatible, hermetically sealed, implantable chamber and fluidically communicated between the drug reservoir and the pump.

3. The apparatus of claim 1 further comprising an MRI compatible inlet safety valve disposed in and hermetically sealed within the MRI compatible, hermetically sealed, implantable chamber and fluidically communicated between the drug reservoir and a refill inlet.

4. The apparatus of claim 1 where the drug reservoir is bellows shaped and resilient, and where the pressure sensor is an MRI compatible reservoir gauge pressure sensor to sense pressure in the drug reservoir, which pressure is correlated with the drug reservoir's volume due to spring loading of the bellows shape of the drug reservoir.

5. The apparatus of claim 1 further comprising a catheter or a ventriculoperitoneal (VP) shunt, and an MRI compatible outlet clog sensor to detect a pressure spike in liquid flow to sense clogging in the catheter or the VP shunt.

6. The apparatus of claim 5 where the VP shunt comprises an optical source and detector to monitor the concentration of medicating agents dispensed from the drug reservoir.

7. The apparatus of claim 1 wherein the MRI compatible refillable drug reservoir is hermetically sealed within the MRI compatible, hermetically sealed, implantable chamber.

8. The apparatus of claim 1 where the pump is remotely programmable to adjust the delivery of medicating agents.

9. The apparatus of claim 1 where the control electronics comprises a microprocessor and a memory programmable for dispensing medicating agents, and for controlling, regulating, and reporting of biological response parameters arising from the medicating agents.

10. The apparatus of claim 1 where the drug reservoir is selectively loaded with biological response modifiers (BRMs), enzymes, therapeutic agents, drugs, and chemotherapy agents.

11. The apparatus of claim 1 further comprising a VP shunt, wherein the VP shunt is configured to irrigate a solid tumor in a patient and wherein the drug reservoir is loaded with an agent to increase cell adhesion molecules targeting the solid tumor used for adherence of cytotoxic cells to the solid tumor.

12. The apparatus of claim 1 where the control electronics includes remotely programmable control circuitry with stored look-up-tables to selectively deliver an optimal biological dose (OBD) as opposed to a maximum tolerated dose (MTD).

13. The apparatus of claim 1 where the drug reservoir is loaded with a chemotherapeutic agent, where the control electronics includes remotely programmable control circuitry incorporating stored pharmacokinetic and pharmacodynamic parameters associated with the chemotherapeutic agent, and where the pump is controlled by the programmable control circuitry to deliver the chemotherapeutic agent in view of the incorporated pharmacokinetic and pharmacodynamic parameters to achieve a desired result without any toxic side effect.

14. The apparatus of claim 1 where the control electronics includes remotely programmable control circuitry to regulate dispensation of tumor BRMs according to their pleiotropic nature to allow for biological processes or mechanisms to develop by selectively reducing or enhancing selected tumor BRMs in the drug reservoir to provide patient-specific treatment.

15. The apparatus of claim 1 where the control electronics includes remotely programmable control circuitry to dispense agents within a specific time domain to a tumor site to selectively provide an immune modulating effect and/or anti-proliferate effect, and dosing depending on which effect is to be maximally stimulated.

16. The apparatus of claim 1 where the control electronics includes remotely programmable control circuitry selectively controlling the pump to provide maximum dosing of a chemotherapeutic agent to a tumor site by using the MTD in a time domain which does not interfere with the activity of BRMs.

17. The apparatus of claim 1 where the control electronics includes remotely programmable control circuitry to allow an expression of a BRM cascade effect due to communication of cytokines as messengers with their synergistic, additive or antagonistic interactions that affect a target tumor cell.

18. The apparatus of claim 1 where the control electronics includes remotely programmable control circuitry to schedule delivery of medicating agents, including chemotherapy agents and BRMs, based on toxicity, measures of bioavailability, solubility, and concentration, and of circulation based on locality.

19. The apparatus of claim 1 where the control electronics includes remotely programmable control circuitry to selectively deliver agents in selective doses on a selective schedule based on individual differences of various tumors depending on the disease stage, immune factors, body weight, age and chronobiology.

20. The apparatus of claim 1 where the control electronics includes remotely programmable control circuitry to mitigate factors such as peak serum concentration associated with peak occurrence of side effects of an agent intravenously injected, so that the peak concentration of the agent is correlated clinically with a peak side effect.

21. The apparatus of claim 1 where the control electronics includes remotely programmable control circuitry to selectively deliver an agent having a bell-shaped response curve as concentration of the agent increases to provide improved control of the use of the agent according to the bell-shaped response curve.

22. The apparatus of claim 1 where the control electronics includes remotely programmable control circuitry to provide an effective mode of administrating an agent in combination with chemotherapy by selectively scheduling delivery local administration of different agents in combination with monoclonal antibodies and tumor necrosis factors (TFNs).

23. The apparatus of claim 1 where the control electronics includes remotely programmable control circuitry to selectively control or exploit delivery, dose, cycle, circadian time effects and the entire pharmacokinetic and pharmacodynamic behavior of an agent and to provide corresponding feedback reports in terms of a biological measure of tumor responses to the agent.

24. The apparatus of claim 1 where the control electronics includes remotely programmable control circuitry to provide local administration of BRMs and chemotherapeutic agents to enhance mechanisms that support overlapping effects in reducing tumor burden and elimination of tumors, to induce an improved response by using biomodulators augmenting patient anti-tumor response via production of cytokines, to decrease suppressor mechanisms, to increase patient immunological response, to limit toxicity of an agent by locality of delivery, to maximize the dose, to increase susceptibility of a cell membrane characteristic for an improved chemotherapy result, or to decrease tumor metastasis.

25. The apparatus of claim 1 where the control electronics includes remotely programmable control circuitry use a Creech technique of regional or isolated limb perfusion to selectively delivery high-doses of chemotherapy to an isolated or local site of melanoma or sarcoma by using BRMs and TNF-α to damage neovascular circulation surrounding a tumor without destroying normal tissue.

26. The apparatus of claim 1 where the control electronics includes remotely programmable control circuitry to selectively deliver a plurality of agents using a corresponding selectively determined plurality of doses and a corresponding selectively determined plurality of schedules of the plurality of agents to maximize the anti-tumor effects of each agent while not increasing toxicity.

27. An apparatus comprising:
an MRI compatible refillable drug reservoir;
an MRI compatible, hermetically sealed, implantable chamber defined between a fluidic plate and a cap;
an MRI compatible refill inlet disposed in and hermetically sealed within the MRI compatible, hermetically sealed, implantable chamber and fluidically communicated to the drug reservoir;
an MRI compatible pump hermetically sealed to the fluidic plate and fluidically communicated to the drug reservoir;
MRI compatible control electronics coupled to a mid layer disposed within the hermetically sealed within the MRI compatible, hermetically sealed, implantable chamber, the MRI compatible control electronics electrically communicated to the pump;
an MRI compatible catheter electrically communicated with the MRI compatible control electronics and fluidically communicated with the pump; and
an MRI compatible ventriculoperitoneal (VP) shunt electrically and fluidically communicated with the catheter; and
a pressure sensor and an outlet clog sensor, where each of the refill inlet, the pressure sensor, and the outlet clog sensor are coupled to the fluidic plate,
where the mid layer comprises a plurality of holes defined therein, where each of the plurality of holes accommodate a respective one of the refill inlet, the pressure sensor, and the outlet clog sensor, and
where the pressure sensor and the outlet clog sensor are electrically communicated to the MRI compatible control electronics coupled to the mid layer.

* * * * *